| United States Patent [19] | [11] | 4,411,906 |
|---|---|---|
| Girijavallabhan et al. | [45] | Oct. 25, 1983 |

[54] (5R,6S,8R)-6-(1-HYDROXYETHYL)-2-(2-FLUOROETHYLTHIO)-PENEM-3-CARBOXYLATES

[75] Inventors: Viyyoor M. Girijavallabhan, Parsippany; Stuart W. McCombie, West Orange; Ashit K. Ganguly, Upper Montclair, all of N.J.

[73] Assignee: Schering Corporation, Kenilworth, N.J.

[21] Appl. No.: 324,931

[22] Filed: Nov. 25, 1981

[51] Int. Cl.³ .................. C07D 499/00; A61K 31/425
[52] U.S. Cl. .............................. 424/270; 260/245.2 R
[58] Field of Search ..................... 260/239.1, 245.2 R; 424/246, 270, 271

[56] References Cited

U.S. PATENT DOCUMENTS 4,260,618  4/1981  Christensen et al. ............... 424/263
4,301,074  11/1981  Christensen et al. ........ 260/245.2 R

FOREIGN PATENT DOCUMENTS 55-153789  11/1980  Japan .
2013674A  8/1979  United Kingdom .

*Primary Examiner*—Nicholas S. Rizzo
*Attorney, Agent, or Firm*—Anita W. Magatti; Carver C. Joyner; Bruce M. Eisen

[57] ABSTRACT

Disclosed herein are (5R,6S,8R)-6-(1-hydroxyethyl)-2-(2-fluoroethylthio)-penem-3-carboxylic acid and the metabolisable esters thereof and alkali metal salts thereof, which are potent antibacterial agents.

21 Claims, No Drawings

(5R,6S,8R)-6-(1-HYDROXYETHYL)-2-(2-FLUOROETHYLTHIO)-PENEM-3-CARBOXYLATES

This invention relates to (5R,6S,8R)-6-(1-hydroxyethyl)-2-(2-fluoroalkylthio)-penem-3-caboxylic acid, to alkali metal salts thereof, to metabolisable esters thereof, to compositions for their use and to methods of using them as antibacterial agents. More particularly, this invention relates to compounds of the formula:

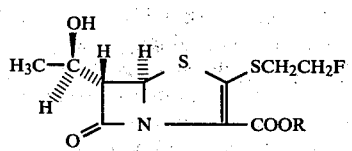

wherein R is a member of the group consisting of hydrogen, a pharmaceutically acceptable cation and a metabolisable ester group;

The pharmaceutically acceptable cations referred to above include alkali metal salts such as sodium and potassium, alkaline earth metal salts, e.g. calcium, as well as ammonium cations such as N-methylglucamine, pyridinium, triethylammonium or triethanolammonium. The sodium and potassium salts are among the preferred embodiments.

The term "metabolisable ester" group denotes a pharmaceutically acceptable ester group which is metabolically removed in the body. Two particularly useful metabolisable ester groups are the phthalidyl group and the pivaloyloxymethyl group.

The compounds of this invention possess several centers of chirality. The present invention is directed to compounds of the preferred stereochemical configuration of formula I wherein the carbon atoms at the 5,6 and 8 positions are of the absolute stereochemistry R, S and R, respectively. The two hydrogen atoms attached to the 5 and 6 carbon atoms are thus trans to one another.

The 2-fluoroethylthiopenem of formula I wherein R is a protecting group, preferably an allyl protecting group, and wherein the 8-hydroxy group is protected, e.g. by a trichloroethoxycarbonyl group, is prepared from the corresponding 2-hydroxyethylthiopenem by reaction with diethylaminosulfur trifluoride (DAST) as described herein in Example 1E. After removal of the 6-(1-trichloroethoxycarbonyl) protecting group, (e.g. by reaction with zinc in acetic acid), the allyl protecting group is removed utilizing procedures described by S. W. McCombie in co-pending application Ser. No. 002,472, filed Jan. 10, 1979, (of common assignee as the instant application), the disclosure of which is incorporated herein by reference. When hexanoic acid is used to remove the allyl protecting group, there is formed a compound of formula I wherein R is hydrogen; whereas, when sodium or potassium hexanoate is used, there is formed a compound of formula I wherein R is sodium or potassium, respectively.

Other pharmaceutically acceptable salts of formula I may be prepared from the sodium salt by methods known in the art such as replacement by ion exchange of an aqueous solution of the sodium salts. Similarly, metabolisable esters of formula I, e.g. the pivaloyloxymethyl and phthalidyl esters may be prepared from the sodium salts utilizing known procedures.

The requisite intermediate, i.e. (5R,6S,8R)-6-(1-hydroxyethyl)-2-(2-hydroxyethylthio)penem-3-carboxylic acid having hydroxy and carboxy protecting groups are preferably prepared via a sterospecific synthesis described herein in Examples 1A-1D, which utilized procedures of Adriano Afonso and Frank Hon, U.S. Ser. No. 230,774 filed Feb. 2, 1981 (of common assignee as the instant application), the disclosure of which is incorporated by reference. The requisite chiral intermediate, methyl (5R,6S,8R)-2,2-dimethyl-6-(1-trichloroethoxycarbonyloxyethyl)penam-3-carboxylate is prepared via known procedures such as described in E.P.O. Published Application No. 0013662.

The compounds of this invention possess antibacterial activity of both the gram-positive and gram-negative type. Most importantly, they are orally active antibacterial agents which afford good blood levels at antibacterial dosages. When tested in standardized microbiological assays, the compounds of this invention are active against such gram-positive organisms as Staphylococcus epidermidis, and Bacillus subtilis and such gram-negative organisms as E. coli and Salmonella at test levels of 0.1 to 100 g/ml. Additionally, they show activity against such organisms which produce beta-lactamases, e.g., penicillanase and cephalosporinase, indicating a resistance against these enzymes. For instance, sodium (5R,6S,8R)-6-(1-hydroxyethyl)-2-(2-fluoroethylthio)-penem-3carboxylate and the corresponding potassium salt are active against Staphylococcus 7607010 at a test level of 0.5 g/ml. When tested against B. subtilis 1119601 (a beta-lactamase-containing organism), these compounds exhibit activity at 0.06 g/ml.

Thus, the present invention includes within its scope pharmaceutical compositions comprising an antibacterially effective amount of a penem of formula I together with a compatible pharmaceutically acceptable carrier or coating. The compounds of formula 1 may be the only antibacterial agent in the pharmaceutical dosage forms, or it may be admixed with other compatible antibacterial agents and/or enzyme inhibitors.

Also included within this invention is the method of effectively treating a warm-blooded animal having a susceptible bacterial infection which comprises administering to said animal a non-toxic antibacterially effective amount of a compound of formula I. Preferred embodiments concern the oral pharmaceutical compositions and the oral administration of such compositions. A particularly preferred embodiment relates to a pharmaceutical composition which is an oral antibacterial dosage unit comprising an antibacterially effective amount of a compound of formula I, e.g., sodium (5R,6S,8R)-6-(1-hydroxyethyl)-2-(2-fluoroethylthio)-penem-3-carboxylate, together with a compatible pharmaceutically acceptable carrier. Of these compositions, those which are solid are particularly useful.

The dosage administered of the penems of this invention is dependent upon the age and weight of the animal species being treated, the exact mode of administration, and the type and severity of bacterial infection being prevented or reduced. Typically, the dosage administered per day will be in the range of 5 to 200 mg/kg per day with 20 to 80 mg/kg per day being preferred.

For oral administration, the compounds of this invention may be formulated in the form of tablets, capsules, elixirs or the like. Likewise, they may be admixed with animal feed. They may also be applied topically in the form of ointments, both hydrophilic and hydrophobic, in the form of lotions which may be aqueous, non-aqueous or of the emulsion type, or in the form of creams.

The compounds of formula I may be utilized in liquid form such as solutions, suspensions, and the like for otic and optic use and may also be administered parenterally via intramuscular injection.

The preferred compositions of this invention relate to oral dosage forms of the preferred compounds of this invention, i.e., compounds of formula I wherein R is sodium or potassium. These oral dosage forms are characterized by an unusual combination of high potency of prolonged duration, broad antibacterial spectrum and efficacy via the oral route of administration.

The following example describes in detail the compounds of this invention and processes for their preparation. It will be apparent to those skilled in the art that many modifications, both of material and method may be practiced without departing from the spirit or scope of the invention.

EXAMPLE I (A)

(3S,4R,5R)-3-(1-Trichloroethoxycarbonyloxyethyl)-4-(2-Hydroxyethylthiocarbothioylthio)Azetidin-2-One Dissolve 10 g of methyl-(5R,6S,8R)-2,2-dimethyl-6-(1-trichloroethoxycarbonyloxyethyl)-penam-3-carboxylate in 150 ml of methylene chloride at 0°–5° C., add 7.36 ml of sulfuryl chloride and stir for one hour at room temperature. Pour the reaction mixture into an excess of aqueous sodium bicarbonate with stirring. Separate the two liquid phases, dry the organic phase and evaporate to a residue. Dissolve the residue in 100 ml of methylene chloride and treat with ozone at $-78°$ C. until a blue color persists, add 5 ml of dimethyl sulfide to the reaction mixture at room temperature and stir for one hour, then add this mixture to a stirred ice cold trithiocarbonate solution prepared from 10 ml of beta-mercaptoethanol and 6 g of potassium hydroxide in 200 ml of 50% aqueous ethanol cooled to 0° C., and treated with 28 ml of carbon disulfide. Allow the mixture of the chlorolactam and the trithiocarbonate solution to react at 0° C. for 45 minutes with stirring, then dilute with water. Extract the reaction mixture with methylene chloride, wash with aqueous sodium bicarbonate, dry over magnesium sulfate and evaporate to a residue. Chromatograph on silica gel, eluting with an increasing concentration of ethyl ether in methylene chloride to 30%. Combine like fractions containing the title compound as determined by thin layer chromatography and evaporate to obtain the product of this step as a light yellow oil.

Yield-8.1 g.

I.R. ($CH_2Cl_2$) 3550, 1770, 1750 cm$-$1.

(B)

(3S,4R,5R)-3-(1-Trichloroethoxycarbonyloxyethyl)-4-[2-(t-Butyldimethylsiloxy)Ethylthiocarbothioylthio]-Azetidin-2-One Dissolve 7.07 g of the product from Step A in a mixture of 50 ml of methylene chloride and 1.43 ml of pyridine, 2.64 g of t-butylchlorodimethylsilane and 0.1 g of imidazole. Stir the solution at room temperature for two days, wash with water and evaporate to a residue. Chromatograph the residue on silica gel using dichloromethane:hexane and then methylene chloride with increasing concentrations of ethyl ether. Combine like fractions containing the title compound as determined by thin layer chromatography and evaporate to obtain the title compound as a light yellow oil.

Yield-8.4 g.

I.R. 3400, 1700 and 1750 cm$-$1.

(C) Allyl-(5R,6S,8R)-2-[2-(t-Butyldimethylsilyloxy)Ethylthio]-6-(1-Trichloroethoxycarbonyloxyethyl)-Penem-3-Carboxylate Dissolve 8.4 g of the product of Step B in 50 ml of methylene chloride containing 2.69 g of allyl oxalyl chloride and stir at 0°–5° C. while adding 2.32 g of diisopropylethylamine in 15 ml of methylene chloride dropwise. Stir the reaction mixture for an additional half-hour at 0°–5° C., wash with water, with dilute hydrochloric acid and with dilute aqueous sodium bicarbonate. Dry the organic solvent phase over magnesium sulfate, filter and evaporate to a residue. Dissolve the residue in 100 ml of ethanol-free chloroform, add 1.0 g of calcium carbonate and reflux with stirring during the addition of 5 g of triethyl phosphite over a 3-hour interval. Reflux the solution for an additional 18 hours, cool and chromatograph on silica gel eluting with methylene chloride:hexane, methylene chloride and finally with 1% ethyl ether in methylene chloride. Combine like fractions containing the title compound as determined by thin layer chromatography to obtain thereby the title compound as a yellowish oil. $^1$H NMR ($CDCl_3$): 0.10 (s,6), 0.92 (s,9), 1.54 (d,3,J=7), 3.07 (n,2), 3.84 (m,3), 4.76 (m,2), 4.79 (s,2), 5.1–5.6 (m,3), 5.64 (d,1,J=2.5) and 5.7—6.2 (m,1).

(D)

Allyl-(5R,6S,8R)-2-(2-Hydroxyethylthio)-6-(1-Trichloroethoxycarbonyloxyethyl)-Penem-3-Carboxylate Dissolve 4.46 g of the product of Step C in a mixture of 32 ml of tetrahydrofuran, 4 ml of water and 4 ml of acetic acid. Stir the solution for 18 hours at room temperature with 2.4 g of tetra-n-butylammonium fluoride. Pour the reaction mixture into a two-phase solvent system consisting of methylene chloride and water with stirring. Wash the organic phase with aqueous sodium bicarbonate. Dry the organic phase over magnesium sulfate, filter and evaporate to a residue. Chromatograph the residue on silica gel using ethyl ether:methylene chloride as the eluant. Combine like fractions containing the title compound as determined by thin layer chromatography and evaporate to obtain thereby the title compound of this example as a yellowish oil.

Yield-2.9 g.

$^1$H NMR ($CDCl_3$): 1.49 (d,3,J=7), 2.17 (m,1,exch by $D_2O$), 3.12 (m,Z), 3.70–4.0 (m,3), 4.72 (m,2), 4.76 (s,2), 5.1–5.6 (m,3), 5.67 (d,2J=2.5) and 5.7–6.2 (m,1).

(E)

Allyl(5R,6S,8R)-2-(2-Fluoroethylthio)-6-(1-Trichloroethoxycarbonyloxyethyl)-Penem-3-Carboxylate Dissolve 400 mg of the product of Step D and 1 g of calcium carbonate in 25 ml of methylene chloride at $-78°$ C. Add 0.35 ml of diethylaminosulfur trifluoride (DAST) and stir for ½ hour. Dilute with ethyl acetate. Stir with water for five minutes at 0° C. Separate layers and wash the organic solvent layer with water. Concentrate the organic layer to a residue and chromatograph on silica gel using ethyl ether: methylene chloride as the eluant. Combine the fractions containing like products as determined by thin layer chromatography and evaporate to obtain the title product.

Yield 200 mg.

NMR 6.2-5.8 (1H,m); 5.7 (1H,d J=1 cps); 5.5-5.3 (3H); 4.85 (1H, J=6 cps and 50 cps); (F-CH coupling);

3.95 (1H, d,d, J=1 cps)-9 cps; 3.25 [tt(S-CH$_2$)]; 1.4 (3H, d, J=9 cps).

I.R. 1795 cm$^{-1}$, 1765 cm$^{-1}$, 1695 cm$^{-1}$.

(F)

Allyl(5R,6S,8R)-2-(2-Fluoroethylthio)-6-(1-Hydroxyethyl)-Penem-3-Carboxylate

Dissolve 200 mg of the product of Step E in 10 ml of tetrahydrofuran. Add 300 mg of zinc, 0.5 ml of acetic acid and 0.5 ml of water. Stir the mixture at −5° to 0° C. for 1½ hours. Extract with ethyl acetate, wash the extract with aqueous calcium carbonate solution and filter. Concentrate the ethyl acetate solution to a residue and chromatograph on a silica gel column using 10% ethyl acetate/methylene chloride as the eluant. Combine the fractions containing like products as determined by thin layer chromatography. Evaporate the combined fractions to obtain thereby the title product.

Yield 100 mg.

NMR 6.2–5.8 (1H, m); 5.7 (1H,d,J=1.5 cps); 5.5–5.3 (2H); 4.9 (1H, J=7 and 50 cps); 4.35 (1Ht,J=50 cps); 3.75 (1H,dd,J=1.5 and 9 cps); 3.3 (2H,m); 1.4 (3H,d,J=9 cps).

I.R. 3400 cm$^{-1}$, 1795 cm$^{-1}$, 1720 cm$^{-1}$ and 1695 cm$^{-1}$.

(G)

Sodium(5R,6S,8R)-2-(2-Fluoroethylthio)-6-(1-Hydroxyethyl)-Penem-3-Carboxylate

Dissolve 86 mg of the product of Step F in 10 ml of methylene chloride. Add 48 mg of sodium hexanoate, 28 mgs of tetrabis (triphenylphosphine) palladiun and 30 mg of triphenylphosphine. Stir the reaction mixture under nitrogen for ½ hour. Extract the methylene chloride with water. Separate the layers. Treat the organic (methylene chloride) layer with phosphoric acid to convert the palladium salt of the penem to the free acid. Extract with ethyl acetate, wash with water, treat the water layer with 8 mg of sodium bicarbonate and add the aqueous layer to the previously obtained aqueous layer and lyophilize. Dissolve the so-called penem salt in 3.0 ml of water and, using pressure, force the aqueous phase through C$_{18}$ silica gel followed by a water wash. Lyophilize the aqueous column eluate and wash to obtain thereby the title compound.

Yield 30 mgs.

$[\alpha]_D^{26}$ = +150.8° [H$_2$O]

NMR, D$_2$O 5.75, 1H, d (J=1 Hz); 5.05 and 4.4 (2 triplets —CH$_2$—F) 2H, (J=1.8 Hz, 9 Hz); 4.3, 1H, m; 3.95, 1H, dd, J=1 and 8 Hz; 3.3, 2H m; 2.2, 1H (EXCHANGABLE-OH); 1.3, 3H, d, J=9 Hz.

In a similar manner, when sodium hexanoate of Step G, Example 1 is replaced by an equivalent quantity of hexanoic acid the corresponding penem carboxylic acid is produced i.e. (5R,6S,8R)-2-(2-fluoroethylthio)-6-(1-hydroxyethyl)-penem-3-carboxylic acid.

Other pharmaceutically acceptable alkali metal salts (e.g. potassium) may be prepared from the sodium salt by methods generally known in the art, such as replacement by ion exchange of an aqueous solution of the sodium salt or by treating a penem carboxylic acid with base having the desired cation. In either event, the pharmaceutically acceptable salt is preferably isolated by lyophilization.

As previously stated, the compounds of this invention are antibacterially effective against strains of both Gram (+) and Gram (−) bacteria. Examples 2 through 8 which follow are directed to some of the dosage forms which may be employed to administer the compounds of this invention. In the formulations the word "Drug" means sodium or potassium salts of (5R,6S,8R)-6-(1-hydroxyethyl)-2-(2-fluoroethylthio)-penem-3-carboxylic acid or an equivalent amount of the free 3-carboxylic acid compound or the phthalidyl or pivaloyloxymethyl esters thereof.

EXAMPLE 2

Injection Formulation Per vial: sodium or potassium (5R,6S,8R)-6-(1-hydroxyethyl)-2-(2-fluoroethylthio)-penem-3-carboxylate (Sterile powder). Exemplary unit dosages may be 125 mg., 250 mg., 500 mg., 1 gm. and 2 gms. Add sterile water for injection U.S.P. or bacteriostatic water for injection U.S.P., for reconstitution.

EXAMPLE 3

Capsule Formulation

| Item No. | Ingredient | mg/capsule | mg/capsule |
|---|---|---|---|
| 1 | Drug | 250 | 500 |
| 2 | Microcrystalline Cellulose | 30 | 60 |
| 3 | Corn Starch, Dried | 15 | 30 |
| 4 | Silica Gel | 4.5 | 9 |
| 5 | Magnesium Stearate | 0.5 | 1 |
| | | 300.0 mg | 600 mg |

Method

Mix Item Nos. 1,2,3 and 4 in a suitable mixer for 10–15 minutes. Add Item No. 5 and mix for 1–3 minutes. Fill the above mixture in two-piece hard gelatin capsules of required size. Alternatively, mix Item Nos. 1,2,3 and 4 in a suitable mixture for 10–15 minutes. Add half the amount of Item No. 5, mix for 1–3 minutes. Pass the mixture through a suitable compactor. Pass the impacted mixture through a suitable mill equipped with 16 mesh screen. Remix and add the remainder amount of Item No. 5. Mix for 1–3 minutes. Fill the above mixture in two-piece hard gelatin capsules of required size.

EXAMPLE 4

Tablet Formulation

| Item No. | Ingredient | mg/tablet | mg/tablet |
|---|---|---|---|
| 1 | Drug | 250 | 500 |
| 2 | Microcrystalline Cellulose | 100 | 200 |
| 3 | Corn Starch, Dried | 40 | 80 |
| 4 | Silica Gel | 6 | 12 |
| 5 | Magnesium Stearate | 4 | 8 |
| | | 400 mg | 800 mg |

Method

Mix Item Nos. 1,3 and half the amount of Item No. 4 in a suitable mixer for 10–15 minutes. Add half the amount of Item No. 5 and mix for 1–3 minutes. Pass the mixture through a suitable compactor. (Alternatively, slug the mixture on a rotary tablet machine equipped with 1" flat bevelled punches). Mill the compacted material or the slugs using a suitable milling machine equipped with 16 mesh screen. Remix. Add Item No. 2 and the remainder amount of Item No. 4. Mix for 10–15 minutes. Add the balance of Item No. 5 and mix for 1–3 minutes. Compress the mixture into the tablets of required shape and size on a rotary tablet machine. The tablets may be coated using standard coating procedures.

EXAMPLE 5

Topical Formulation

| Item No. | Ingredient | mg/g |
|---|---|---|
| 1 | Drug | 25 |
| 2 | Ethyl Alcohol | 400 |
| 3 | Hydroxypropyl Cellulose | 15 |
| 4 | Polyethylene Glycol 400 | 560 |

Mix Item Nos. 1,2, and 4 in a suitable mixer. Stir vigorously and charge Item No. 3. Maintain stirring until uniformity is achieved.

EXAMPLE 6

Oral Powder for Reconstitution (I)

Part A (Powder Formulation)

| Item No. | Ingredient | mg/g |
|---|---|---|
| 1 | Drug | 46.3 |
| 2 | Flavor(s) | q.s. |
| 3 | Colorant | q.s. |
| 4 | Preservative | q.s. |
| 5 | Buffering Agents | q.s. |
| 6 | Saccharin | 28.3 |
|  | To make | 1.0 g |

Mix Item Nos. 1,2,3,4, and 5 thoroughly, Charge Item No. 6 and mix until uniformity is achieved.

Part B (Reconstitution)

Charge 54 g of above formulated powder into a proper container and add enough water to make up 100 ml. Shake well after the addition of water. Each 5 ml (1 teaspoonful) will then contain drug equivalent to 125 mg.

EXAMPLE 7

Oral Liquid

| Item No. | Ingredient | mg/ml |
|---|---|---|
| 1 | Drug | 25.0 |
| 2 | Sweetener | q.s. |
| 3 | Flavor | q.s. |
| 4 | Colorant | q.s. |
| 5 | Vegetable Oil | q.s. |
|  | To make | 1.0 ml |

Charge 90% of Item No. 5 needed into a suitable container. Charge Item Nos. 1,2,3 and 4 and mix well. Bring to the final volume by the reserved Item No. 5.

EXAMPLE 8

Suppository

| Item No. | Ingredient | Suppository |
|---|---|---|
| 1 | Drug | 125.0 |
| 2 | Witepsol H-15 | 1868 |

Melt Item No. 2 and blend Item No. 1 until uniform. Pour into mold and congeal in refrigerator. Remove suppository from mold.

We claim:

1. A compound of the formula:

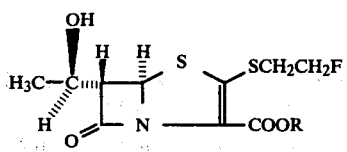

wherein R is a member of the group consisting of hydrogen, a pharmaceutically acceptable cation and a metabolisable ester group.

2. A compound of claim 1 wherein R is sodium, said compound being sodium (5R,6S,8R)-6-(1-hydroxyethyl)-2-(2-fluoroethylthio)-penem-3-carboxylate.

3. A compound of claim 1 wherein R is potassium, said compound being potassium (5R,6S,8R)-6-(1-hydroxyethyl)-2-(2-fluoroethylthio)-penem-3-carboxylate.

4. A compound of claim 1 wherein R is a metabolisable ester.

5. A compound of claim 4 wherein R is phthalidyl, said compound being phthalidyl (5R,6S,8R)-6-(1-hydroxyethyl)-2-(2-fluoroethylthio)-penem-3-carboxylate.

6. A compound of claim 4 wherein R is pivaloyloxymethyl, said compound being pivaloyloxymethyl (5R,6S,8R)-6-(1-hydroxyethyl)-2-(2-fluoroethylthio)-penem-3-carboxylate.

7. A compound of claim 1 wherein R is hydrogen, said compound being (5R,6S,8R)-6-(1-hydroxyethyl)-2-(2-fluoroethylthio)-penem-3-carboxylic acid.

8. A pharmaceutical composition comprising an antibacterially effective amount of a compound of claim 1 together with a non-toxic pharmaceutically acceptable carrier.

9. An oral dosage form comprising an antibacterially effective amount of a compound of claim 1 in combination with a pharmaceutically acceptable carrier.

10. A dosage form according to claim 9 wherein the antibacterial compound is sodium (5R,6S,8R)-6-(1-hydroxyethyl)-2-(2-fluoroethylthio)-penem-3-carboxylate.

11. A dosage form according to claim 9 wherein the antibacterial compound is potassium (5R,6S,8R)-6-(1-hydroxyethyl)-2-(2-fluoroethylthio)-penem-3-carboxylate.

12. A dosage form according to claim 9 wherein the antibacterial compound is (5R,6S,8R)-6-(1-hydroxyethyl)-2-(2-fluoroethylthio)-penem-3-carboxylic acid.

13. A dosage form according to claim 9 wherein the antibacterial compound is phthalidyl (5R,6S,8R)-6-(1-hydroxyethyl)-2-(2-fluoroethylthio)-penem-3-carboxylate.

14. A dosage form according to claim 9 wherein the antibacterial compound is pivaloyloxymethyl (5R,6S,8R)-6-(1-hydroxyethyl)-2-(2-fluoroethylthio)-penem-3-carboxylate.

15. A method of effectively treating a warm blooded animal having a susceptible bacterial infection which comprises administering to said animal a non-toxic, antibacterially effective amount of a compound of claim 1.

16. A method according to claim 15 wherein the administration is by the oral route.

17. A method according to claim 16 wherein the compound being administered is sodium (5R,6S,8R)-6-

(1-hydroxyethyl)-2-(2-fluoroethylthio)-penem-3-carboxylate.

18. A method according to claim 16 wherein the compound being administered is potassium (5R,6S,8R)-6-(1-hydroxyethyl)-2-(2-fluoroethylthio)-penem-3-carboxylate.

19. A method according to claim 16 wherein the compound being administered is phthalidyl (5R,6S,8R)-6-(1-hydroxyethyl)-2-(2-fluoroethylthio)-penem-3-carboxylate.

20. A method according to claim 16 wherein the compound being administered is pivaloyloxymethyl (5R,6S,8R)-6-(1-hydroxyethyl)-2-(2-fluoroethylthio)-penem-3-carboxylate.

21. A method according to claim 16 wherein the compound being administered is (5R,6S,8R)-6-(hydroxyethyl)-2-(2-fluoroethhylthio)-penem-3-carboxylic acid.

* * * * *